United States Patent
Grass et al.

(10) Patent No.: US 6,426,989 B2
(45) Date of Patent: Jul. 30, 2002

(54) COMPUTED TOMOGRAPHY METHOD

(75) Inventors: Michael Grass, Hamburg; Thomas Koehler, Norderstedt; Roland Proksa, Hamburg, all of (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/840,206

(22) Filed: Apr. 23, 2001

(30) Foreign Application Priority Data

Apr. 29, 2000 (DE) .......................................... 100 21 219

(51) Int. Cl.⁷ ............................................... G01N 23/00
(52) U.S. Cl. ........................................... 378/4; 378/901
(58) Field of Search ............................... 378/4–20, 901

Primary Examiner—Craig E Church
(74) Attorney, Agent, or Firm—John Vodopia (57) ABSTRACT

The invention relates to a computed tomography method which involves a conical radiation beam which irradiates the examination zone along at least two trajectories that are offset relative to one another in the direction of the axis of rotation, the distance between the trajectories being chosen to be so large that voxels in an intermediate region are not completely irradiated neither in one trajectory nor in the other trajectory. The absorption distribution in this intermediate region can be reconstructed without loss of image quality when measuring data from both trajectories are combined.

7 Claims, 5 Drawing Sheets

COMPUTED TOMOGRAPHY METHOD

The invention relates to a computed tomography method which includes the steps of:

- generating, using a radiation source, a conical radiation beam that traverses an examination zone or an object present therein,
- generating relative motions between the radiation source on the one side and the examination zone or the object on the other side, which relative motions include a rotation about an axis of rotation along a first, closed trajectory and along at least a second trajectory which is identical to the first trajectory but offset in the direction of the axis of rotation,
- acquiring, while using a detector unit, measuring data that is dependent on the intensity in the radiation beam to the other side of the examination zone during the relative motions,
- reconstructing the absorption distribution in the examination zone.

The invention also relates to a computed tomography apparatus as well as to a computer program for controlling such a computed tomography apparatus.

The use of a conical radiation beam instead of a fan-shaped beam offers the advantage that a larger part of the examination zone (measured in the direction of the axis of rotation), or of the object present therein, can be covered and reproduced by means of a single rotation along the closed trajectory. Should an even larger part of the examination zone be imaged, such a rotation should be succeeded at least once by a relative motion in the direction of the axis of rotation and the examination zone should be irradiated and imaged from a second trajectory. The shift must be selected to be so large that imaging can take place without gaps.

According to a method that is known from German patent application 19 843 812.5 (PHD 98-111), the shift may be so large that the voxels in an intermediate region are not continuously exposed to X-rays neither from the one trajectory nor from the other trajectory. The reconstruction of the absorption distribution in this intermediate region is then realized in that only measuring data which is associated with a radiation angle range of only 180° (relative to the voxel) is taken into account for each voxel. It is a drawback of this method that the absorption distribution in the intermediate region can be reconstructed only with a less favorable signal-to-noise ratio and with additional artefacts, that is, in comparison with the absorption distribution in the regions that are continuously exposed to radiation during the rotation of the radiation source along the trajectories.

Granted, this drawback could be avoided by choosing the shift between the trajectories to be so small that the regions of the object that are continuously exposed to radiation from one of the trajectories directly adjoin one another. This leads to an increased radiation load when the method is used for a medical examination, but at least to increased thermal loading of the radiation source. Moreover, the acquisition time required for scanning a part of the examination zone that is selected in the direction of the axis of rotation is thus prolonged.

It is an object of the present invention to provide a method of the kind set forth such that on the one hand a suitable image quality is obtained and on the other hand a low dose load or short acquisition time for covering a given part of the examination zone.

This object is achieved in accordance with the invention by selecting the distance between the trajectories to be such that:

- on the one hand voxels that are temporarily not exposed to any radiation during the two relative motions are present in an intermediate region between the trajectories, and
- on the other hand the radiation source projects both trajectories continuously on the detector unit in such a manner that the projections intersect the lateral edge of the area of the detector unit that is used for the acquisition of measuring data, and
- the absorption distribution in the intermediate region being reconstructed while taking into account measuring data acquired during the two relative motions.

Thus, in conformity with the invention there are not only the regions whose absorption can be completely measured from one of the trajectories but also an intermediate region in which such measurement is not possible, because the voxels in this region are not irradiated by the radiation source during the entire rotation along the trajectory. The invention is based on the recognition of the fact that the angular ranges wherefrom a voxel in the intermediate region is irradiated from both trajectories together amount to at least 360° in the case of the stated selection of the distance of the trajectories, so that the absorption distribution in the intermediate region can also be reconstructed with an image quality which is comparable to that attained for the regions whose absorption distribution is reconstructed from the measuring data acquired along a single trajectory, provided that measuring data from both trajectories are used for the reconstruction.

Preferably, the distance between the neighboring trajectories is chosen in conformity with claim 2. This choice of the distance is optimum. When a smaller distance is chosen, the radiation load is increased or the measuring time is prolonged whereas in the case of a larger distance (the projection of one trajectory on the detector unit then no longer intersects the lateral edge of the area of the detector unit that is used for the acquisition of measuring data) it is no longer possible to reconstruct the absorption distribution in the intermediate region without loss of image quality.

Claim 3 discloses a preferred reconstruction method that involves an amount of calculation work that is small in comparison with other methods and yields a very high image quality. The reconstruction of the absorption in the intermediate region then utilizes filtered data of groups acquired from different trajectories. This reconstruction method is known per se from German patent application . . . (PHD 98-123) or from the article by Graβ, Kohler, Proksa "3D cone-beam CT reconstruction for circular trajectories" in Phys. Med. Biol 45 (2000) 329-347. The version of the method that is disclosed in claim 4 enables a particularly simple reconstruction.

Claim 5 discloses a computed tomography apparatus for carrying out the method in accordance with the invention. The preferred embodiment disclosed in claim 6 ensures, in conjunction with the reconstruction method claimed in claim 3 and using the distance defined in claim 2, that the edge of the radiation beam and the projection of the one trajectory on the detector unit coincide. In that case each voxel between the two trajectories receives exactly as much radiation as required for the desired image quality.

Claim 7 defines a computer program for controlling a computed tomography apparatus as claimed in claim 5.

The invention will be described in detail hereinafter with reference to the drawings. Therein.

Figure 1:
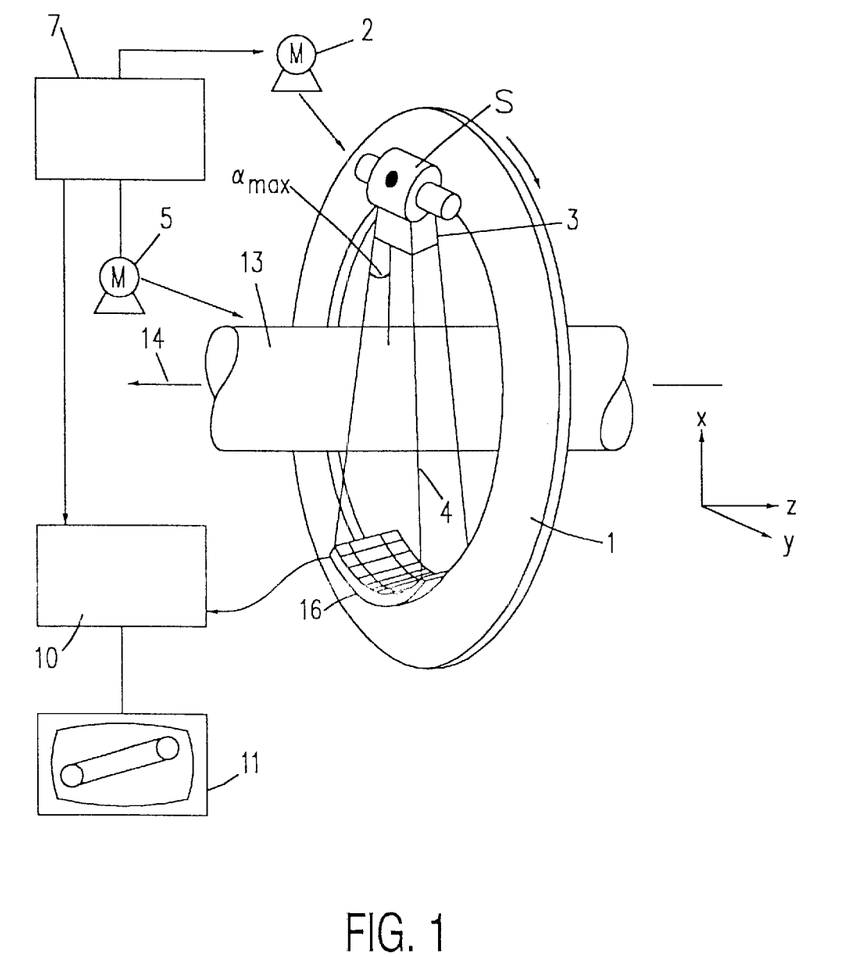
FIG. 1 shows a computed tomography apparatus that is suitable for carrying out the method in accordance with the invention.

The computed tomography apparatus shown in FIG. 1 includes a gantry 1 that is capable of rotation about an axis of rotation 14 in a direction parallel to the z direction of the co-ordinate system shown in FIG. 1. To this end, the gantry is driven by a motor 2 at a preferably constant but adjustable angular speed. A radiation source S, for example an X-ray source, is mounted on the gantry. The X-ray source is provided with a collimator arrangement 3 which forms a conical radiation beam 4 from the radiation produced by the radiation source S, that is, a radiation beam having a finite dimension other than zero in the z direction as well as in a direction perpendicular thereto (that is, in a plane perpendicular to the axis of rotation).

The radiation beam 4 traverses an examination zone 13 in which an object, for example a patient on a patient table (both not shown), may be present. The examination zone 13 is shaped as a cylinder. After having traversed the examination zone 13, the X-ray beam 4 is incident on a two-dimensional detector unit 16 which is mounted on the gantry 1 and includes a number of detector rows, each of which includes a plurality of detector elements. The detector rows are situated in planes extending perpendicularly to the axis of rotation, preferably on an arc of a circle around the radiation source S; however, they may also have a different shape, for example, they may describe an arc of a circle around the axis of rotation 14 or may be linear. Each detector element struck by the radiation beam 4 delivers a measuring value for a ray of the radiation beam 4 in any position of the radiation source.

The angle of aperture of the radiation beam 4, denoted by the reference $\alpha_{max}$ (the angle of aperture is defined as the angle enclosed by a ray that is situated at the edge of the radiation beam 4 in a plane perpendicular to the axis of rotation relative to a plane defined by the radiation source S and the axis of rotation 14), then determines the diameter of the object cylinder in which the object to be examined is situated during the acquisition of the measuring values. The examination zone 13, or the object or the patient table, can be displaced parallel to the axis of rotation 14 or the z axis by means of a motor 5. Analogously, however, the gantry could also be displaced in this direction.

When the motors 5 and 2 run simultaneously, the radiation source S and the detector unit 16 describe a helical trajectory relative to the examination zone 13. However, when the motor 5 for the displacement in the z direction is inactive and the motor 2 rotates the gantry, a circular trajectory is obtained for the radiation source S and the detector unit 16 relative to the examination zone 13. For the sake of simplicity only the realization of such a circular trajectory will be considered hereinafter, even though other closed trajectories, for example, elliptical trajectories or trajectories that are inclined relative to the axis of rotation are also feasible.

The measuring data acquired by the detector unit 16 is applied to an image processing computer 10 which reconstructs the absorption distribution in a part of the examination zone 13 therefrom for display, for example, on a monitor 11. The two motors 2 and 5, the image processing computer 10, the radiation source S and the transfer of the measuring data from the detector unit 16 to the image processing computer 10 are controlled by a control unit 7.

Figure 2:
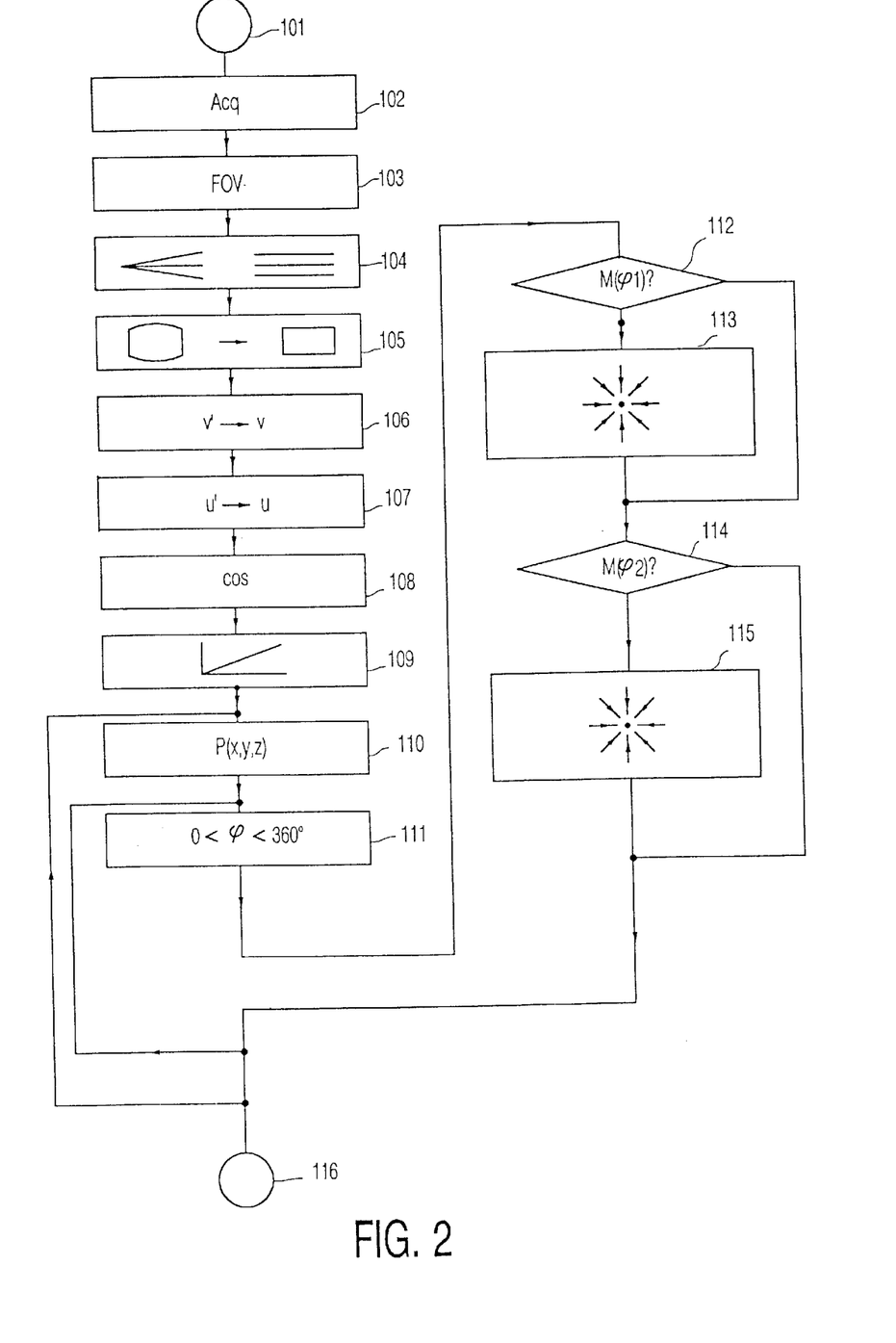
FIG. 2 shows a flow chart illustrating the method in accordance with the invention.

FIG. 2 shows the execution of a measuring and reconstruction method that can be carried out by means of the computed tomography apparatus shown in FIG. 1.

After the initialization in the block 101, the gantry rotates at a constant angular speed. In the step 102 the diameter of the FOV (field of view) to be reproduced is defined. The diameter may correspond to the maximum diameter of the examination zone 13 as defined by $\alpha_{max}$, but may also be smaller.

In the step 103 the radiation of the radiation source S is switched on and the measuring values acquired by the detector elements of the detector unit 16 along this first trajectory are stored in a memory of the image processing computer 10. Subsequently, the object, or the examination zone 13, on the one side and the gantry 1 with the radiation source S and the detector unit 16 on the other side are displaced relative to one another over a distance d (while the X-rays are switched off). The gantry subsequently rotates at a constant angular speed again (along a second trajectory in relation to the examination zone). The X-rays are switched on again and the measuring values then acquired by the detector elements of the detector unit are stored again in the memory of the image processing computer 10.

Figure 3:
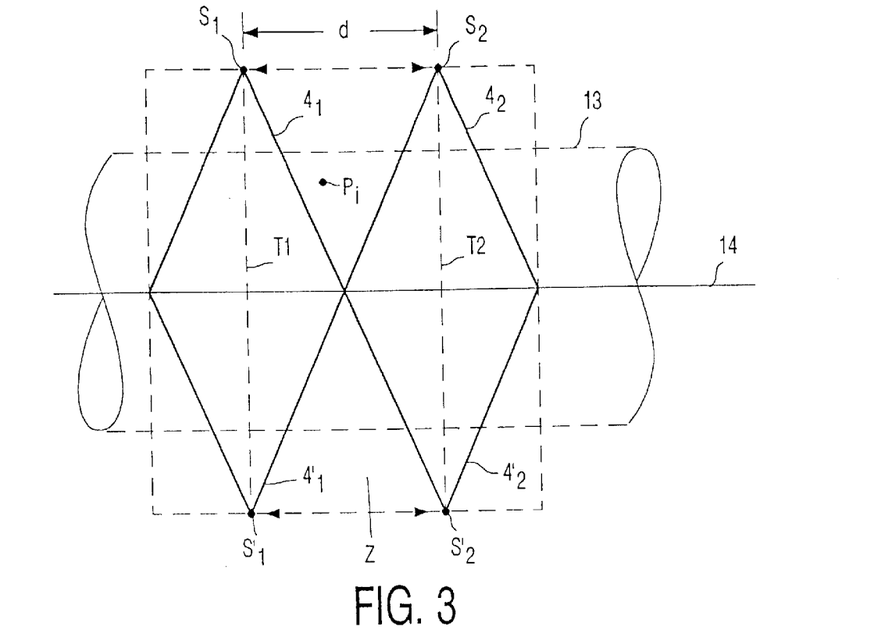
FIG. 3 shows the situation of the trajectories relative to one another and to the examination zone.

FIG. 3 shows the situation of the circular trajectories T1 and T2 along which the radiation source S moves relative to the examination zone 13. For the sake of simplicity it is assumed that the gantry, or the trajectory, has been shifted and that the object stood still; however, this is irrelevant, because the only essential aspect is the relative displacement between the examination zone 13 on the one side and the gantry on the other side.

The circular trajectories T1 and T2 appear as (dashed) lines while the axis of rotation 14 is situated in the plane of drawing in the rendition of FIG. 3. Moreover, the radiation source (denoted by a dot) is also shown in the highest position ($S_1$ and $S_2$) and in the lowest position ($S'_1$ and $S'_2$) on each trajectory. The associated radiation beam ($4_1$ and $4_2$ or $4'_1$ and $4'_2$, respectively) is represented in solid lines for each of these positions. The trajectories are situated at a distance d from one another.

Two disc-shaped regions that are defined by the radiation beams $4_1$ and $4_2$ and $4'_1$ and $4'_2$, respectively, can be recognized in FIG. 3. In these regions the absorption distribution can be completely reconstructed by means of the measuring data acquired along one of the two trajectories. Therebetween there is situated a region Z. During the travel of the radiation source along the trajectories, the voxels in this intermediate region are temporarily not struck by radiation. For example, the voxel $P_i$ is not exposed to radiation from the radiation source positions $S_1$ and $S_2$.

Figure 4:
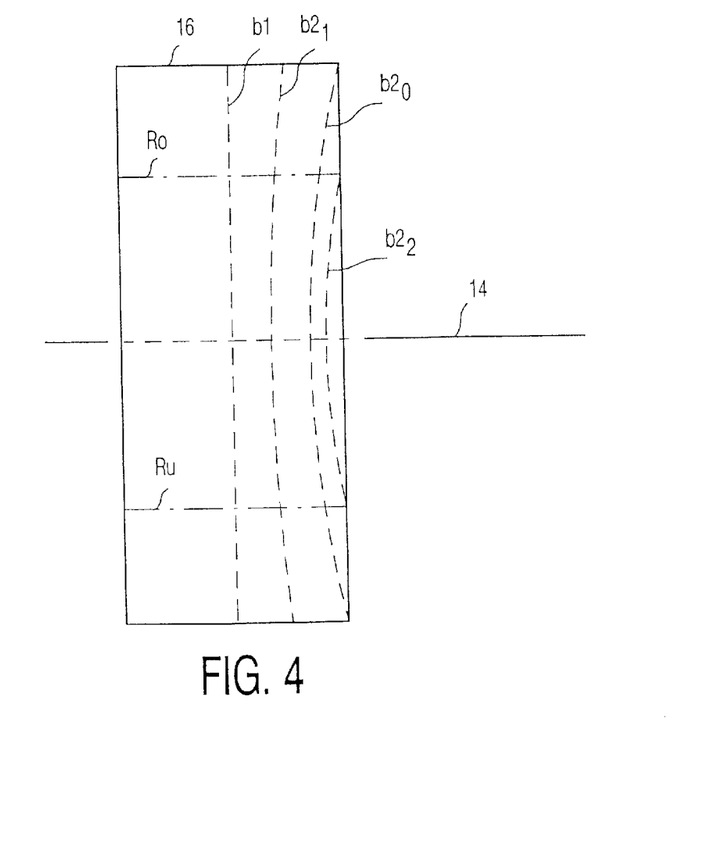
FIG. 4 shows the projection of the trajectories on the detector unit.

The selection of the distance d in order to ensure that the absorption distribution can also be reconstructed in the region Z will be described in detail hereinafter with reference to FIG. 4. FIG. 4 shows the projection of both trajectories on the detector unit 16. This rendition is based on the assumption that the immaterial trajectories can be projected onto the detector unit (in a geometrical context such a projection, however, can be simply assumed) and that the detector unit 16 is situated on one of the trajectories, for example, on the left-hand trajectory T1.

The projection of the trajectory T1 is denoted by the reference b1. As is shown in FIG. 4, it is identical to the central line of the detector unit, assuming that the detector unit 16 extends symmetrically relative to the trajectory. The trajectory T2 is in principle projected to the right of the trajectory T1 on the detector unit 16 (in the case of a shift to the right), its distance from the projection b1 being larger as the distance d of the trajectory T2 is larger. When the detector unit 16 describes an arc of a circle around the radiation source S, as previously assumed, these projections are curved. FIG. 4 shows three different projections for three different distances d between the trajectory T2 and the trajectory T1:

When the distance d is chosen to be such that the projection b2$_1$ is obtained, the entire examination zone between T1 and T2 can be reconstructed; however, this distance is not yet optimum, because it would make the radiation dose unnecessarily high and the reconstructed region unnecessarily short.

The optimum distance d$_{opt}$ (for the case where the complete cross-section of the examination zone 13 is to be imaged) is obtained when the projection of the trajectory T2 extends through the corners of the detector unit, that is, as for the projection b2$_0$. In that case the region between the trajectories can still be imaged and the distance d is larger than in the case of the projection b2'$_1$.

When the distance is chosen to be even larger, the projection b2$_2$ is obtained. This projection no longer intersects the lateral edges of the detector unit (situated at the top and the bottom in FIG. 4), but only the right-hand edge. In this case it is no longer possible to reconstruct the entire cross-section of the examination zone between the two trajectories completely.

However, when an object having a diameter that is smaller than the examination zone 13 is examined and the angle of aperture of the radiation beam 4 is reduced in a plane perpendicular to the axis of rotation, complete reconstruction of the absorption distribution in the examination zone of reduced diameter may still be possible in this case. A condition to be satisfied in this respect is that the radiation beam 4 should irradiate only the part of the detector unit whose boundaries are denoted by the references Ro and Ru, so that the projection b2$_2$ extends exactly through the corner points of the area of the detector unit that is used for the acquisition of measuring data.

The optimum distance d$_{opt}$ for which complete reconstruction of the absorption distribution is possible, therefore, is calculated in conformity with the following formule:

$$d_{opt} = s \tan \gamma \cos \beta.$$

Therein, s is the distance between the radiation source S and the axis of rotation, γ is the cone angle (being half the angle of aperture of the radiation beam 4 in a plane containing the axis of rotation 14) and β is the fan angle (being half the angle of aperture of the radiation beam 4 in a plane perpendicular to the axis of rotation 14).

Figure 5:
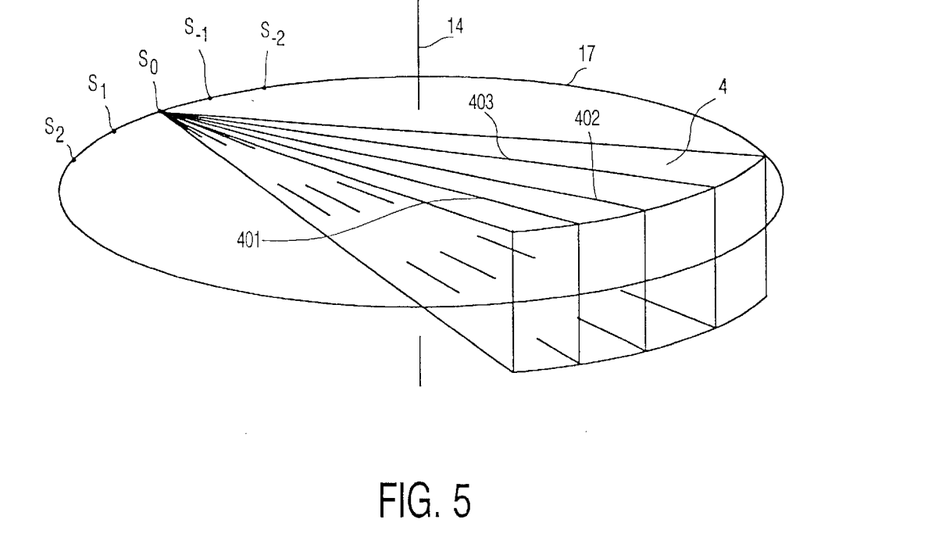
FIG. 5 shows a conical radiation beam generated in a radiation source position.

FIG. 5 shows the circular trajectory (for example, the trajectory T1) along which the radiation source S and the detector unit 16 move about the axis of rotation 14. The radiation beam 4 is shown for a given radiation source position S$_0$. This conical radiation beam 4 may be assumed to be composed of a plurality of flat fan beams which are situated in planes parallel to the axis of rotation 14, like the fan beams 401 . . . 403. Even though the rays of the conical radiation beam 4 can also be combined in a different manner, hereinafter the term "fan beam" will be used only for rays that are situated in a common plane parallel to the axis of rotation. Such fan beams emanate from a radiation source position and are detected by a respective column of detector elements on the detector unit 16 that extends parallel to the axis of rotation 14. FIG. 5 shows that the emitted, conical radiation beam 4 was also measured in other positions of the radiation source (for example, S$_{-1}$, S$_1$ or S$_2$).

A rebinning operation is performed in the steps 104 to 107. The data acquired along the two trajectories is then resorted and re-interpolated as if it had been formed by means of a different radiation source (a circular radiation source emitting mutually parallel fan beams) and a different detector (a flat, rectangular "virtual" detector containing the axis of rotation 14).

First of all, in the step 104 the fan beams from different radiation source positions, being situated in mutually parallel planes, are then combined so as to form respective groups. The fan beams associated with a group, therefore, satisfy the condition that the sum of the angles χ and δ should have the same value for all fan beams of this group. Therein, χ is the angle enclosed by the plane of the fan beam relative to a plane defined by the radiation source position and the axis of rotation and is given by the position of the column of detector elements having measured the relevant fan beam. δ is an angle characterizing the radiation source position (for example, S$_0$) on the circle 17. When the fan beams do not exactly satisfy this condition for a radiation source position, a corresponding fan beam must be determined for this radiation source position by interpolation from the rays of neighboring fan beams.

Figure 6:
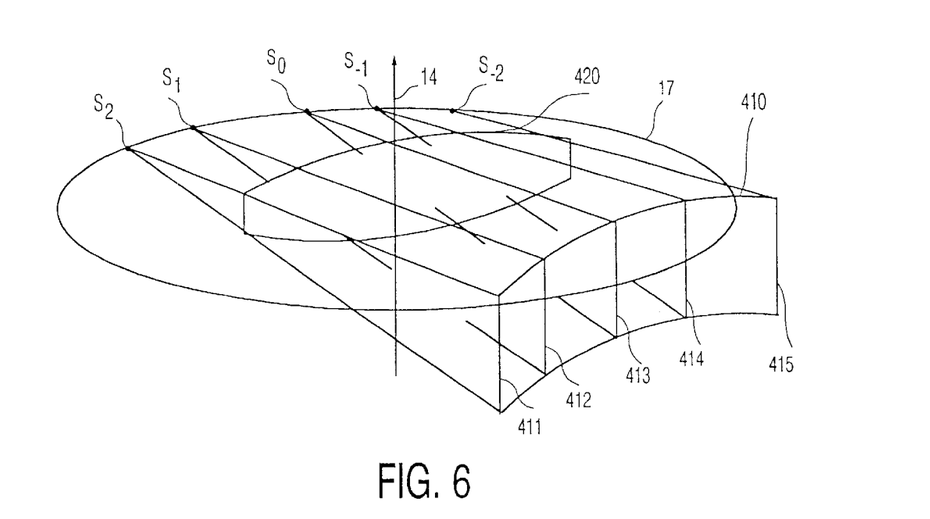
FIG. 6 shows the fan beams formed in parallel planes by the rebinning.

FIG. 6 shows a group of fan beams thus formed. Each time one fan beam from each of the neighboring radiation source positions S$_{-2}$ . . . S$_0$ . . . S$_2$ belongs to a respective group. Each group can be characterized by the angle 8 of the radiation source position (for example, S$_0$) whose fan beam belonging to the group traverses the axis of rotation 14 (generally speaking, this is the central radiation source position, so the radiation source position S$_0$ in the example shown in FIG. 6). In that case there may be as many groups of fan beams as there are radiation source positions, but also more or less groups.

The fan beams thus determined, including the fan beams 411 . . . 415 shown in FIG. 6, define a radiation beam 410 that has a tent-like shape and is composed of fan beams situated in planes that extend parallel to one another and to the axis of rotation. FIG. 6 also shows the region of intersection 420 which occurs when the radiation beam 410 is intersected by a plane which contains the axis of rotation 14 and extends perpendicularly to the planes of the fan beams 411 . . . 415.

Figure 7:
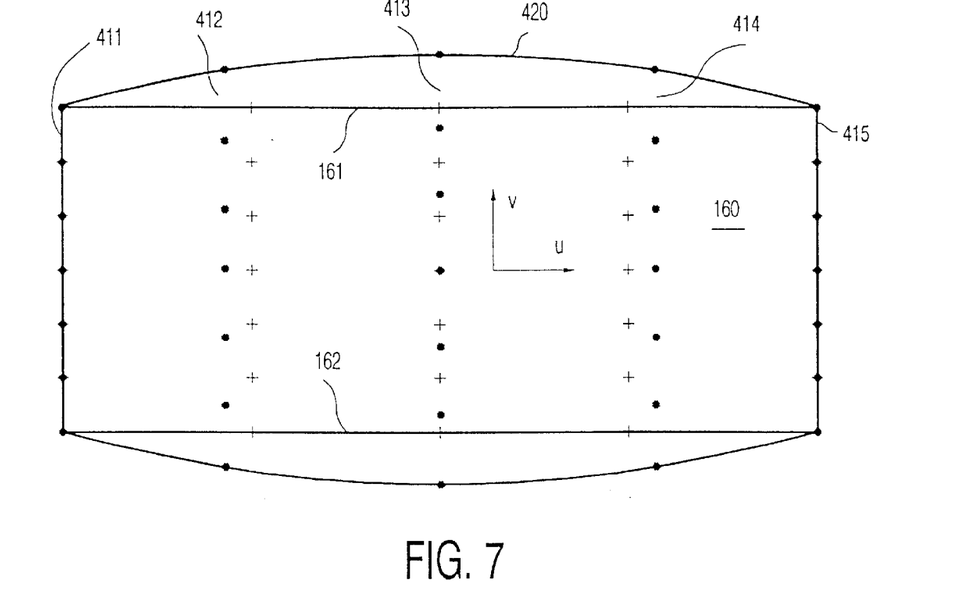
FIG. 7 is a cross-sectional view of said fan beams.

As appears notably from FIG. 7, showing this region of intersection, the upper and lower edges (offset relative to one another in the direction of the axis of rotation) are curved. This curvature is due to the fact that the radiation source positions at the center (for example, S$_0$) are situated further from the plane of intersection than the radiation source position at the edge (S$_2$ or S$_{-2}$) and that the fan beams all have the same angle of aperture, because the detector rows describe an arc of a circle around the radiation source S. In the case of a different geometry of the detector rows, the shape of the plane of intersection 420 would be different. In the case of a flat detector unit (for example, having linear detector rows) the curvature would even be more pronounced, because the fan beams situated at the edge (for example, 411 and 415) would then have a smaller angle of aperture.

For each group of fan beams a rectangular virtual detector is defined in the flat region of intersection 420 (step 105), the upper edge and the lower edge 161 and 162 of said detector being defined by the dimensions of the outer fan beams 411 and 415, respectively, in the flat plane of intersection. When the trajectories are situated at the optimum distance $d_{opt}$ from one another, for example, the edge 161 of a virtual detector of the one trajectory contacts exactly the edge 162 of a virtual detector of the other trajectory.

When the diameter of the FOV to be reconstructed is chosen to be smaller than the diameter of the examination zone 13, the respective outer fan beams (for example, 411, 415) of each group can be dispensed with. The distance between the upper and the lower edges 161 and 162, and hence the optimum distance $d_{opt}$ of the trajectories T1 and T2, can in that case be chosen so as to be larger than in the example shown in FIG. 7.

FIG. 7 also shows (marked by round dots) the piercing points of some rays, contained in the fan beams 411 . . . 415, through this virtual detector. Finally, crosses denote the supporting points of a regular cartesian grid. Generally speaking, the piercing points and the supporting points do not coincide. It appears that at the periphery the fan beams are situated nearer to one another than at the center (for example, 402 is nearer to 411 than to 413) and that the piercing points of the rays of a fan beam are situated further from one another at the center (for example, at 413) than at the periphery (for example, 415). Therefore, in the two subsequent steps 106 and 107 the measuring values at the equidistant supporting points within the virtual detector 160 must be determined from the measuring values for the piercing points.

First of all, in the step 106 a vertical interpolation is performed in such a manner that in the vertical direction of all fan beams the supporting points are situated at the same distance from one another as the piercing points or supporting points at the edge of the virtual detector 160. In the step 107 an interpolation is performed in the horizontal direction, so that interpolated values are obtained for supporting points that are situated at the same distance from one another in the horizontal direction within the virtual detector 160. The interpolation steps 106 and 107 can also be performed in the reverse order or can even be combined.

As a result of this interpolation in the horizontal direction and the vertical direction, the intensity of the radiation is present at the equidistant supporting points of a regular Cartesian grid in the UV co-ordinate system of the virtual detector 160. The supporting points themselves define new fan beams which are situated in parallel planes at the same distance from one another. Only such new fan beams (which may be partly identical to the original fan beams) are used for the further reconstruction.

A part of the rays whose piercing points are situated outside the virtual detector 160 is not used in the steps 106 and 107. Therefore, it is advantageous to construct the collimator in such a manner that as from the very beginning the conical radiation beam 4 does not contain any rays extending above the upper edge 161 or below the lower edge 162 of the virtual detector 160. This results in a further reduction of the radiation dose whereto the patient is exposed.

Instead of linear edges extending perpendicularly to the axis of rotation, the collimator arrangement 3 should have inwards curved edges for this purpose, so that the fan beams that intersect the axis of rotation 14, or are situated at a small distance therefrom, have an angle of aperture that is smaller (measured in a plane parallel to the axis of rotation 14) than fan beams that are situated at the outer edge of the radiation beam. The outer edge of the surface irradiated by such a radiation beam on the detector unit 14 would then coincide with the projection $b2_0$ (see FIG. 4) that extends through the corner point of the area of the detector unit that is used for the acquisition of measuring data.

Subsequently, in the step 108 the data associated with the individual rays is multiplied by a weighting factor which corresponds to the cosine of the angle enclosed by the radiation relative to a normal to the virtual detector 160. The image quality is thus improved.

After completion of the steps 103 to 108, the radiation intensity at the regular supporting points of the virtual detector 160 associated with the relevant group has thus been determined for each group of fan beams. This facilitates the necessary high-pass filtering fundamentally, because only it is only necessary to perform one-dimensional filtering of the data produced on the virtual detector 160 by the rebinning operation. Therefore, in the step 109 this data is subjected to one-dimensional filtering with a transfer factor that increases ramp-like as a function of frequency. To this end, it is merely necessary to take into account the values of the supporting points succeeding one another in the horizontal direction. This filtering is performed for all groups of fan beams produced by the rebinning operation.

The data determined, after the rebinning operation and the filtering, for the beams defined by the supporting points in the virtual window 160 are subsequently used for the reconstruction of the absorption distribution in the examination zone by backprojection.

After selection of a voxel (x,y,z) in the step 110, in the step 111 an angle $\phi$ is selected which defines the fan beams in a plane perpendicular to the axis of rotation. In the step 112 it is checked whether there is a ray that emanates from the first trajectory T1 and extends exactly through the voxel P(x,y,z) at the angle $\phi_1=\phi$. If this is the case, in the step 113 for this voxel P(x,y,z) there is accumulated a contribution which corresponds to the value arising from the filtering operation for this ray in the block 109. However, it may also be that none of the rays of the group defined by the angle $\phi_1$ extends exactly through the voxel P, but that a plurality of rays enclose the voxel. In that case the contribution to be allocated to the point is determined by way of a suitable interpolation of the values allocated to these rays.

After the step 113 (or when the test in the step 112 has produced a negative result), it is checked in the step 114 whether there is a ray that emanates from the second trajectory T2 and extends through the voxel P(x,y,z) at the angle $\phi_2=\phi$, or whether there are a plurality of rays that enclose the voxel at this angle. If this is the case, in the step 115 for this voxel P(x,y,z) there is accumulated a contribution which corresponds to the value (or values) resulting from the filtering operation for this ray (or these rays) in the block 109.

After determination of the contribution to the voxel P for the direction $\phi$, the steps 112 . . . 115 are repeated for a different angle $\phi$. After an angular range of 360° has been completed for $\phi$, the steps 111 . . . 115 are repeated for another voxel P(x,y,z) until an absorption value has been determined for all voxels.

Three situations are then possible:
  When the voxel is situated within the disc-like region that is defined by the trajectory T1 and the radiation beams $4_1$ and $4'_1$ and is rotationally symmetrical relative to the axis 14, it has been irradiated from an angular range of 360° from the trajectory T1. For any angle $\phi$ in the range of from 0 to 360° a contribution to the absorption value of the point P(x,y,z) can be determined (in the step 113) (and be added to the contributions already determined for this voxel), which contribution has been derived exclusively from the measuring values acquired along the first trajectory.

When the voxel is situated within the disc-like region that is defined by the trajectory T2 and the radiation beams $4_2$ and $4'_2$ and is rotationally symmetrical relative to the axis 14, it has been irradiated from an angular range of 360° from the trajectory T2. In that case a contribution to the absorption value of the point P(x,y,z) can be determined for each angle φ in the range of from 0 to 360° (in the step 115), which contribution has been derived exclusively from the measuring values acquired along the second trajectory T2.

However, if the voxel $P_i$ is situated outside said disc-like regions, that is, in the intermediate region Z (for example, like the voxel $P_i$ in FIG. 3), this voxel has not been irradiated from all radiation source positions along the trajectory T1 or the trajectory T2. The contributions to the absorption value of the voxel P(x,y,z), however, can be derived from the measuring values acquired along both trajectories.

Figure 8:
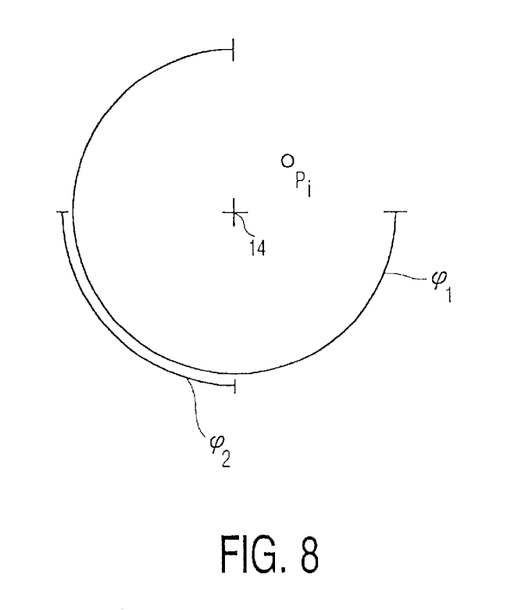
FIG. 8 shows the parts of the trajectories wherefrom a voxel is irradiated relative to this voxel.

The latter case is illustrated in FIG. 8 which shows the axis of rotation 14, extending perpendicularly to the plane of drawing, and the voxel $P_i$. Also shown is the arc $\phi_i$ wherefrom the radiation source on the trajectory T1 can irradiate the relevant voxel. It appears that the voxel $P_i$ cannot be irradiated from the radiation source position situated nearer to this point. It also appears from FIG. 3 that from the lower radiation source positions the point $P_i$ can be covered by the radiation beam $4'_1$, but not by the radiation beam 41 emitted in the radiation source position the point $P_i$ can be covered $S_1$ situated nearer to the point $P_i$.

Finally, FIG. 8 also shows the angular range $\phi_2$ wherefrom the voxel $P_i$ on the trajectory T2 is irradiated (this arc should actually have the same diameter as the arc $\phi_1$; for the sake of clarity, however, the radius of the arc is shown in slightly enlarged form). When the voxel $P_i$ is situated nearer to the trajectory T1, the arc $\phi_i$ is longer than the arc $\phi_2$. When $P_i$ is situated exactly halfway between the two trajectories, the two arcs are of the same length and extend over 180° each. When $P_i$ is situated nearer to the trajectory T2, $\phi_2$ becomes larger than $\phi_1$.

When the distance between the trajectories is chosen in conformity with the equation 5, the sum of the arc angles (viewed from the axis of rotation) is exactly 360°. Therefore, and because it is irrelevant whether the point $P_i$ is irradiated from the bottom left to the top right or from the top right to the bottom left, the measuring data for the voxel $P_i$, acquired on the first trajectory, can be supplemented with data measured at the angle $\phi_2$ on the second trajectory (with $\phi_2=\phi_1°$). For a voxel in the intermediate region Z, therefore, contributions may be provided by the step 113 as well as by the step 115. However, it is alternatively possible that a contribution is made in only one of the steps 113, 115 or that no contribution is made.

After the described reconstruction of the absorption distribution in all voxels P(x,y,z) of the two disc-shaped regions and in the intermediate regions, the method can be terminated (step 116). However, it is also possible to reconstruct additionally the absorption distribution in the adjoining external regions that are denoted by dashed lines in FIG. 3. A method that is suitable in this respect is described in the previously mentioned German patent application . . . (PHD 98-111). However, more artefacts are liable to occur during the reconstruction in this region and the signal-to-noise ratio will be less favorable than in the disc-shaped regions and in the intermediate region.

When the region of relevance to the examination is larger, the measuring data can be reconstructed along more than two trajectories. The region between two neighboring trajectories is then reconstructed each time as described with reference to FIG. 2.

Other reconstruction methods in which the rebinning operation is performed in a different manner are also feasible. However, for the reconstruction of the absorption distribution in the intermediate region it will then be necessary again to take into account measuring data acquired along both trajectories.

What is claimed is:

1. A computed tomography method which includes the steps of generating, using a radiation source (S), a conical radiation beam (4) that traverses an examination zone (13) or an object present therein, generating relative motions between the radiation source (S) on the one side and the examination zone (13) or the object on the other side, which relative motions include a rotation about an axis of rotation (14) along a first, closed trajectory (T1) and along at least a second trajectory (T2) which is identical to the first trajectory but offset in the direction of the axis of rotation, acquiring, while using a detector unit (16), measuring data that is dependent on the intensity in the radiation beam (4) to the other side of the examination zone (13) during the relative motions, reconstructing the absorption distribution in the examination zone (13), characterized in that the distance (d) between the trajectories (T1, T2) is chosen so that on the one hand voxels ($P_i$) that are temporarily not exposed to any radiation during the two relative motions are present in an intermediate region (Z) between the trajectories, and on the other hand the radiation source (S) projects both trajectories (T1, T2) continuously on the detector unit in such a manner that the projections ($b2_0$) intersect the lateral edge of the area of the detector unit (16) that is used for the acquisition of measuring data, and the absorption distribution in the intermediate region (Z) is reconstructed while taking into account measuring data acquired during the two relative motions.

2. A computed tomography method as claimed in claim 1, characterized in that the distance (d) between the trajectories is chosen in such a manner that the projection ($b2_0$, $b2_2$) of one of the two trajectories always extends through at least one corner point of the area of the detector unit that is used for the acquisition of measuring data.

3. A computed tomography method as claimed in claim 1, characterized in that the reconstruction includes the following steps:

a) rebinning the measuring data so as to form a number of groups, each group including a plurality of planes that extend parallel to one another and to the axis of rotation and contain a respective fan beam (411 . . . 415), b) one-dimensional filtering of the data produced by the rebinning operation for each group in the direction perpendicular to the direction of the planes, c) reconstructing the spatial distribution of the absorption by backprojection of the filtered data of a plurality of groups while taking into account filtered data from both trajectories for the backprojection in the intermediate region (Z).

4. A computed tomography method as claimed in claim 3, characterized in that the rebinning operation is performed on a respective virtual detector (160) which extends perpendicularly to the planes of each group, has a flat and rectangular shape and contains the axis of rotation (14).

5. A computed tomography apparatus for carrying out the method claimed in claim 1, including a radiation source, a detector unit which is coupled thereto, a drive arrangement for rotating and/or displacing an object present in the examination zone and the radiation source relative to one another about an axis of rotation or parallel to the axis of rotation, a reconstruction unit for reconstructing the spatial distribution of the absorption within the examination zone from the measuring data acquired by the detector unit, and a control unit for controlling the radiation source, the detector unit, the drive arrangement and the reconstruction unit, characterized in that it also includes means (S, 3) for generating, using a radiation source (S), a conical radiation beam that traverses an examination zone or an object present therein, a first drive unit (2) for generating relative motions, including a rotation about an axis of rotation (14), between the radiation source on the one side and the examination zone (13) or the object on the other side along a first, closed trajectory (T1) and along at least one second trajectory (T2) which is identical to the first trajectory but offset in the direction of the axis of rotation, a second drive unit (5) for displacing the object relative to the radiation source (S) between the relative motions in the direction parallel to the axis of rotation (14) over such a distance (d) that on the one hand voxels (Pi) that are temporarily not exposed to any radiation during the two relative motions are present in an intermediate region (Z) between the trajectories (T1, T2), and on the other hand the radiation source (S) projects both trajectories continuously on the detector unit in such a manner that the projections intersect the lateral edge of the area of the detector unit (16) that is used for the acquisition of measuring data, and means (10) for reconstructing the absorption distribution in the examination zone, the reconstruction in the intermediate region utilizing measuring data acquired during the two relative motions.

6. A computed tomography apparatus for carrying out the method as claimed in claim 5, including a collimator arrangement (3) for generating the radiation beam, characterized in that the edges of the collimator arrangement (3) that are offset in the direction of the axis of rotation (14) are shaped in such a manner that the aperture of the conical radiation beam is smaller at its center than at its edges.

7. A computer program for a control unit (7) for controlling a radiation source (S), a detector unit (16), a drive arrangement and a reconstruction unit (10) of a computed tomography apparatus for carrying out the method claimed in claim 1 as follows:

generating, using a radiation source (S), a conical radiation beam (4) that traverses an examination zone (13) or an object present therein, generating relative motions, including a rotation about an axis of rotation, between the radiation source on the one side and the examination zone or the object on the other side along a first, closed trajectory (T1) and along at least a second trajectory (T2) that is identical to the first trajectory but offset in the direction of the axis of rotation, where on the one hand voxels ($P_i$) which are temporarily not exposed to any radiation during the two relative motions are present in an intermediate region between the trajectories, and on the other hand the radiation source projects both trajectories continuously on the detector unit in such a manner that they intersect the lateral edge of the area of the detector unit that is used for the acquisition of measuring data, and acquiring measuring data, using a detector unit (16), that is dependent on the intensity in the radiation beam to the other side of the examination zone during the relative motions, reconstructing the absorption distribution in the examination zone, the reconstruction in the intermediate region utilizing measuring data acquired during the two relative motions.

* * * * *